United States Patent
Zdeblick

(10) Patent No.: US 8,332,020 B2
(45) Date of Patent: Dec. 11, 2012

(54) TWO-WRIST DATA GATHERING SYSTEM

(75) Inventor: Mark Zdeblick, Portola Valley, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 0 days.

(21) Appl. No.: 13/260,081

(22) PCT Filed: Jan. 28, 2011

(86) PCT No.: PCT/US2011/023017
§ 371 (c)(1),
(2), (4) Date: Sep. 23, 2011

(87) PCT Pub. No.: WO2011/094608
PCT Pub. Date: Aug. 4, 2011

(65) Prior Publication Data
US 2012/0022341 A1 Jan. 26, 2012

Related U.S. Application Data

(60) Provisional application No. 61/300,435, filed on Feb. 1, 2010, provisional application No. 61/378,878, filed on Aug. 31, 2010.

(51) Int. Cl.
*A61B 5/04* (2006.01)
(52) U.S. Cl. ........................ 600/509; 600/300
(58) Field of Classification Search .................. None
See application file for complete search history.

(56) References Cited

U.S. PATENT DOCUMENTS

| | | | |
|---|---|---|---|
| 3,812,854 A | 5/1974 | Michaels et al. | |
| 3,880,146 A | 4/1975 | Everett et al. | |
| 4,403,989 A | 9/1983 | Christensen et al. | |
| 4,475,905 A | 10/1984 | Himmelstrup | |
| 4,487,602 A | 12/1984 | Christensen et al. | |
| 4,529,401 A | 7/1985 | Leslie et al. | |
| 4,551,133 A | 11/1985 | Zegers de Beyl et al. | |
| 4,621,644 A | 11/1986 | Ellers | |
| 4,669,479 A | 6/1987 | Dunseath, Jr. | |
| 4,705,503 A | 11/1987 | Dorman et al. | |
| 4,850,967 A | 7/1989 | Cosmai | |
| 4,911,916 A | 3/1990 | Cleary | |
| 4,922,901 A | 5/1990 | Brooks et al. | |
| 5,006,342 A | 4/1991 | Cleary et al. | |
| 5,125,888 A | 6/1992 | Howard et al. | |
| 5,135,479 A | 8/1992 | Sibalis et al. | |

(Continued)

FOREIGN PATENT DOCUMENTS

JP 6296633 10/1994
(Continued)

OTHER PUBLICATIONS

AADE, "AADE 37th Annual Meeting San Antonio Aug. 4-7, 2010" American Association of Diabetes Educators (2010); http://www.diabeteseducator.org/annualmeeting/2010/index.html; 2 pp.

(Continued)

*Primary Examiner* — Kennedy Schaetzle
(74) *Attorney, Agent, or Firm* — Oppedahl Patent Law Firm LLC

(57) ABSTRACT

Sensing is carried out from locations at considerable remove from the stomach. Cooperating sensor electronics are placed at each of two wrists of the patient. The potential discomfort and inconvenience of an abdominal patch are reduced or eliminated. And alternative power sources become available.

24 Claims, 3 Drawing Sheets

U.S. PATENT DOCUMENTS

| | | | |
|---|---|---|---|
| 5,156,911 A | 10/1992 | Stewart |
| 5,167,649 A | 12/1992 | Zook |
| 5,190,522 A | 3/1993 | Wojcicki et al. |
| 5,205,292 A | 4/1993 | Czar et al. |
| 5,213,568 A | 5/1993 | Lattin et al. |
| 5,246,418 A | 9/1993 | Haynes et al. |
| 5,284,133 A | 2/1994 | Burns et al. |
| 5,300,299 A | 4/1994 | Sweet et al. |
| 5,317,506 A | 5/1994 | Coutre et al. |
| 5,331,953 A | 7/1994 | Andersson et al. |
| 5,351,695 A | 10/1994 | Mills et al. |
| 5,363,842 A | 11/1994 | Mishelevich et al. |
| 5,364,838 A | 11/1994 | Rubsamen |
| 5,394,866 A | 3/1995 | Ritson et al. |
| 5,404,871 A | 4/1995 | Goodman et al. |
| 5,415,866 A | 5/1995 | Zook |
| 5,479,920 A | 1/1996 | Piper et al. |
| 5,487,378 A | 1/1996 | Robertson et al. |
| 5,505,195 A | 4/1996 | Wolf |
| 5,505,958 A | 4/1996 | Bello et al. |
| 5,507,277 A | 4/1996 | Rubsamen et al. |
| 5,509,404 A | 4/1996 | Lloyd et al. |
| 5,522,378 A | 6/1996 | Ritson et al. |
| 5,527,288 A | 6/1996 | Gross et al. |
| 5,536,503 A | 7/1996 | Kitchell et al. |
| 5,540,669 A | 7/1996 | Sage et al. |
| 5,542,410 A | 8/1996 | Goodman et al. |
| 5,556,421 A | 9/1996 | Prutchi et al. |
| 5,570,682 A | 11/1996 | Johnson |
| 5,586,550 A | 12/1996 | Ivri et al. |
| 5,587,237 A | 12/1996 | Korpman |
| 5,593,390 A | 1/1997 | Castellano et al. |
| RE35,474 E | 3/1997 | Woodard et al. |
| 5,608,647 A | 3/1997 | Rubsamen et al. |
| 5,616,124 A | 4/1997 | Hague et al. |
| 5,622,162 A | 4/1997 | Johansson et al. |
| 5,622,180 A | 4/1997 | Tammi et al. |
| 5,634,899 A | 6/1997 | Shapland et al. |
| 5,645,855 A | 7/1997 | Lorenz |
| 5,655,516 A | 8/1997 | Goodman et al. |
| 5,655,523 A | 8/1997 | Hodson et al. |
| 5,656,286 A | 8/1997 | Miranda et al. |
| 5,666,945 A | 9/1997 | Davenport |
| 5,676,129 A | 10/1997 | Rocci, Jr. et al. |
| 5,686,099 A | 11/1997 | Sablotsky et al. |
| 5,688,232 A | 11/1997 | Flower |
| 5,694,919 A | 12/1997 | Rubsamen et al. |
| 5,694,920 A | 12/1997 | Abrams et al. |
| 5,697,899 A | 12/1997 | Hillman et al. |
| 5,709,202 A | 1/1998 | Lloyd et al. |
| 5,713,349 A | 2/1998 | Keaney |
| 5,724,986 A | 3/1998 | Jones, Jr. et al. |
| 5,740,793 A | 4/1998 | Hodson et al. |
| 5,746,711 A | 5/1998 | Sibalis et al. |
| 5,781,442 A | 7/1998 | Engleson et al. |
| 5,794,612 A | 8/1998 | Wachter et al. |
| 5,807,375 A | 9/1998 | Gross et al. |
| 5,809,997 A | 9/1998 | Wolf |
| 5,810,888 A | 9/1998 | Fenn |
| 5,813,397 A | 9/1998 | Goodman et al. |
| 5,823,179 A | 10/1998 | Grychowski et al. |
| 5,826,570 A | 10/1998 | Goodman et al. |
| 5,830,175 A | 11/1998 | Flower |
| 5,839,430 A | 11/1998 | Cama |
| 5,843,014 A | 12/1998 | Lattin et al. |
| 5,848,991 A | 12/1998 | Gross et al. |
| 5,851,197 A | 12/1998 | Marano et al. |
| 5,857,994 A | 1/1999 | Flower |
| 5,860,957 A | 1/1999 | Jacobsen et al. |
| 5,865,786 A | 2/1999 | Sibalis et al. |
| 5,865,787 A | 2/1999 | Shapland et al. |
| 5,873,835 A | 2/1999 | Hastings et al. |
| 5,894,841 A | 4/1999 | Voges |
| 5,906,567 A | 5/1999 | McPhee et at |
| 5,906,579 A | 5/1999 | Vander et al. |
| 5,921,237 A | 7/1999 | Eisele et al. |
| 5,924,997 A | 7/1999 | Campbell |
| 5,925,021 A | 7/1999 | Castellano et al. |
| 5,928,201 A | 7/1999 | Poulsen et al. |
| 5,960,792 A | 10/1999 | Lloyd et al. |
| 5,967,986 A | 10/1999 | Cimochowski et al. |
| 5,967,989 A | 10/1999 | Cimochowski et al. |
| 5,991,655 A | 11/1999 | Gross et al. |
| 5,997,501 A | 12/1999 | Gross et al. |
| 6,006,747 A | 12/1999 | Eisele et al. |
| 6,012,454 A | 1/2000 | Hodson et al. |
| 6,018,680 A | 1/2000 | Flower |
| 6,024,976 A | 2/2000 | Miranda et al. |
| 6,029,083 A | 2/2000 | Flower et al. |
| 6,053,873 A | 4/2000 | Govari et al. |
| 6,053,888 A | 4/2000 | Kong |
| 6,055,980 A | 5/2000 | Mecikalski et al. |
| RE36,754 E | 6/2000 | Noel |
| 6,076,519 A | 6/2000 | Johnson |
| 6,085,740 A | 7/2000 | Ivri et al. |
| 6,085,742 A | 7/2000 | Wachter |
| 6,095,141 A | 8/2000 | Armer et al. |
| 6,105,571 A | 8/2000 | Coffee |
| 6,109,260 A | 8/2000 | Bathe |
| 6,116,233 A | 9/2000 | Denyer et al. |
| 6,119,684 A | 9/2000 | Nohl et al. |
| 6,125,844 A | 10/2000 | Samiotes |
| 6,142,146 A | 11/2000 | Abrams et al. |
| 6,148,815 A | 11/2000 | Wolf |
| 6,152,130 A | 11/2000 | Abrams et al. |
| 6,196,218 B1 | 3/2001 | Voges |
| 6,196,219 B1 | 3/2001 | Hess et al. |
| 6,198,966 B1 | 3/2001 | Heruth |
| 6,202,642 B1 | 3/2001 | McKinnon et al. |
| 6,221,383 B1 | 4/2001 | Miranda et al. |
| 6,231,560 B1 | 5/2001 | Bui et al. |
| 6,237,398 B1 | 5/2001 | Porat et al. |
| 6,237,589 B1 | 5/2001 | Denyer et al. |
| 6,237,594 B1 | 5/2001 | Davenport |
| 6,245,026 B1 | 6/2001 | Campbell et al. |
| 6,251,079 B1 | 6/2001 | Gambale et al. |
| 6,254,573 B1 | 7/2001 | Haim et al. |
| 6,256,533 B1 | 7/2001 | Yuzhakov et al. |
| 6,260,549 B1 | 7/2001 | Sosiak |
| 6,269,340 B1 | 7/2001 | Ford et al. |
| 6,272,370 B1 | 8/2001 | Gillies et al. |
| 6,283,951 B1 | 9/2001 | Flaherty et al. |
| 6,283,953 B1 | 9/2001 | Ayer et al. |
| 6,309,370 B1 | 10/2001 | Haim et al. |
| 6,315,719 B1 | 11/2001 | Rose et al. |
| 6,316,022 B1 | 11/2001 | Mantelle |
| 6,318,361 B1 | 11/2001 | Sosiak |
| 6,327,486 B1 | 12/2001 | Nissila et al. |
| 6,340,357 B1 | 1/2002 | Poulsen et al. |
| 6,352,715 B1 | 3/2002 | Hwang et al. |
| 6,377,848 B1 | 4/2002 | Garde et al. |
| 6,378,520 B1 | 4/2002 | Davenport |
| 6,385,488 B1 | 5/2002 | Flower et al. |
| 6,390,088 B1 | 5/2002 | Nohl et al. |
| 6,394,997 B1 | 5/2002 | Lemelson |
| 6,397,838 B1 | 6/2002 | Zimlich et al. |
| 6,406,426 B1 | 6/2002 | Reuss et al. |
| 6,413,238 B1 | 7/2002 | Maget |
| 6,422,236 B1 | 7/2002 | Nilsson |
| 6,425,392 B1 | 7/2002 | Sosiak |
| 6,427,684 B2 | 8/2002 | Ritsche et al. |
| 6,431,171 B1 | 8/2002 | Burton |
| 6,435,175 B1 | 8/2002 | Stenzler |
| 6,443,146 B1 | 9/2002 | Voges |
| 6,448,303 B1 | 9/2002 | Paul |
| 6,453,195 B1 | 9/2002 | Thompson |
| 6,468,242 B1 | 10/2002 | Wilson et al. |
| 6,484,721 B1 | 11/2002 | Bliss |
| 6,485,461 B1 | 11/2002 | Mason et al. |
| 6,516,796 B1 | 2/2003 | Cox et al. |
| 6,517,481 B2 | 2/2003 | Hoek et al. |
| 6,517,527 B2 | 2/2003 | Gambale et al. |
| 6,520,928 B1 | 2/2003 | Junior et al. |
| 6,527,759 B1 | 3/2003 | Tachibana et al. |
| 6,533,733 B1 | 3/2003 | Ericson et al. |
| 6,536,423 B2 | 3/2003 | Conway |
| 6,540,154 B1 | 4/2003 | Ivri et al. |

| Patent # | Date | Inventors |
|---|---|---|
| 6,564,093 B1 | 5/2003 | Ostrow et al. |
| 6,568,390 B2 | 5/2003 | Nichols et al. |
| 6,575,932 B1 | 6/2003 | O'Brien et al. |
| 6,578,741 B2 | 6/2003 | Ritsche et al. |
| 6,582,393 B2 | 6/2003 | Sage |
| 6,584,971 B1 | 7/2003 | Denyer et al. |
| 6,585,698 B1 | 7/2003 | Packman et al. |
| 6,589,229 B1 | 7/2003 | Connelly et al. |
| 6,599,281 B1 | 7/2003 | Struys et al. |
| 6,605,072 B2 | 8/2003 | Struys et al. |
| 6,606,989 B1 | 8/2003 | Brand et al. |
| 6,607,508 B2 | 8/2003 | Knauer |
| 6,615,827 B2 | 9/2003 | Greenwood et al. |
| 6,629,524 B1 | 10/2003 | Goodall et al. |
| 6,640,804 B2 | 11/2003 | Ivri et al. |
| 6,651,651 B1 | 11/2003 | Bonney et al. |
| 6,655,381 B2 | 12/2003 | Keane et al. |
| 6,656,148 B2 | 12/2003 | Das et al. |
| 6,678,555 B2 | 1/2004 | Flower et al. |
| 6,685,648 B2 | 2/2004 | Flaherty et al. |
| 6,705,316 B2 | 3/2004 | Blythe et al. |
| 6,715,487 B2 | 4/2004 | Nichols et al. |
| 6,723,077 B2 | 4/2004 | Pickup et al. |
| 6,726,661 B2 | 4/2004 | Munk et al. |
| 6,728,574 B2 | 4/2004 | Ujhelyi et al. |
| 6,745,761 B2 | 6/2004 | Christrup et al. |
| 6,745,764 B2 | 6/2004 | Hickle |
| 6,746,429 B2 | 6/2004 | Sadowski et al. |
| 6,748,945 B2 | 6/2004 | Grychowski et al. |
| 6,796,956 B2 | 9/2004 | Hartlaub et al. |
| 6,807,965 B1 | 10/2004 | Hickle |
| 6,810,290 B2 | 10/2004 | Lebel et al. |
| 6,854,461 B2 | 2/2005 | Nichols et al. |
| 6,858,011 B2 | 2/2005 | Sehgal |
| 6,866,037 B1 | 3/2005 | Aslin et al. |
| 6,886,557 B2 | 5/2005 | Childers et al. |
| 6,893,415 B2 | 5/2005 | Madsen et al. |
| 6,902,740 B2 | 6/2005 | Schaberg et al. |
| 6,923,784 B2 | 8/2005 | Stein et al. |
| 6,941,168 B2 | 9/2005 | Girouard et al. |
| 6,949,081 B1 | 9/2005 | Chance |
| 6,958,691 B1 | 10/2005 | Anderson et al. |
| 6,971,383 B2 | 12/2005 | Hickey et al. |
| 6,981,499 B2 | 1/2006 | Anderson et al. |
| 6,983,652 B2 | 1/2006 | Blakley et al. |
| 6,985,771 B2 | 1/2006 | Fischell et al. |
| 6,985,870 B2 | 1/2006 | Martucci et al. |
| 6,990,975 B1 | 1/2006 | Jones et al. |
| 6,999,854 B2 | 2/2006 | Roth |
| 7,010,337 B2 | 3/2006 | Furnary et al. |
| 7,034,692 B2 | 4/2006 | Hickle |
| 7,040,314 B2 | 5/2006 | Nguyen et al. |
| 7,044,911 B2 | 5/2006 | Drinan et al. |
| 7,047,964 B2 | 5/2006 | Bacon |
| 7,054,782 B2 | 5/2006 | Hartlaub |
| 7,072,802 B2 | 7/2006 | Hartlaub |
| 7,089,935 B1 | 8/2006 | Rand |
| 7,097,853 B1 | 8/2006 | Garbe et al. |
| 7,104,972 B2 | 9/2006 | Moller et al. |
| 7,107,988 B2 | 9/2006 | Pinon et al. |
| 7,108,680 B2 | 9/2006 | Rohr et al. |
| 7,117,867 B2 | 10/2006 | Cox et al. |
| 7,138,088 B2 | 11/2006 | Wariar et al. |
| 7,147,170 B2 | 12/2006 | Nguyen et al. |
| 7,168,597 B1 | 1/2007 | Jones et al. |
| 7,181,261 B2 | 2/2007 | Silver et al. |
| 7,191,777 B2 | 3/2007 | Brand et al. |
| 7,198,172 B2 | 4/2007 | Harvey et al. |
| 7,201,734 B2 | 4/2007 | Hickle |
| 7,204,823 B2 | 4/2007 | Estes et al. |
| 7,220,240 B2 | 5/2007 | Struys et al. |
| 7,225,805 B2 | 6/2007 | Bacon |
| 7,232,435 B2 | 6/2007 | Hildebrand et al. |
| 7,242,981 B2 | 7/2007 | Ginggen |
| 7,247,154 B2 | 7/2007 | Hickle |
| 7,261,733 B1 | 8/2007 | Brown et al. |
| 7,267,121 B2 | 9/2007 | Ivri et al. |
| 7,278,983 B2 | 10/2007 | Ireland et al. |
| 7,291,126 B2 | 11/2007 | Shekalim |
| 7,320,675 B2 | 1/2008 | Pastore et al. |
| 7,322,352 B2 | 1/2008 | Minshull et al. |
| 7,322,355 B2 | 1/2008 | Jones et al. |
| 7,331,340 B2 | 2/2008 | Barney |
| 7,342,660 B2 | 3/2008 | Altobelli et al. |
| 7,347,200 B2 | 3/2008 | Jones et al. |
| 7,347,202 B2 | 3/2008 | Aslin et al. |
| 7,347,851 B1 | 3/2008 | Kriksunov |
| 7,367,968 B2 | 5/2008 | Rosenberg et al. |
| 7,380,550 B2 | 6/2008 | Sexton et al. |
| 7,382,263 B2 | 6/2008 | Danowski et al. |
| 7,383,837 B2 | 6/2008 | Robertson et al. |
| 7,387,121 B2 | 6/2008 | Harvey |
| 7,390,311 B2 | 6/2008 | Hildebrand et al. |
| 7,397,730 B2 | 7/2008 | Skyggebjerg et al. |
| 7,415,384 B2 | 8/2008 | Hartlaub |
| 7,424,888 B2 | 9/2008 | Harvey et al. |
| 7,455,667 B2 | 11/2008 | Uhland et al. |
| 7,458,373 B2 | 12/2008 | Nichols et al. |
| 7,467,629 B2 | 12/2008 | Rand |
| 7,483,743 B2 | 1/2009 | Mann et al. |
| 7,488,305 B2 | 2/2009 | Mickley et al. |
| 7,495,546 B2 | 2/2009 | Lintell et al. |
| 7,510,551 B2 | 3/2009 | Uhland et al. |
| 7,517,332 B2 | 4/2009 | Tonelli et al. |
| 7,520,278 B2 | 4/2009 | Crowder et al. |
| 7,530,352 B2 | 5/2009 | Childers et al. |
| 7,530,975 B2 | 5/2009 | Hunter |
| 7,537,590 B2 | 5/2009 | Santini et al. |
| 7,542,798 B2 | 6/2009 | Girouard |
| 7,544,190 B2 | 6/2009 | Pickup et al. |
| 7,548,314 B2 | 6/2009 | Altobelli et al. |
| 7,549,421 B2 | 6/2009 | Levi et al. |
| 7,552,728 B2 | 6/2009 | Bonney et al. |
| 7,554,090 B2 | 6/2009 | Coleman et al. |
| 7,575,003 B2 | 8/2009 | Rasmusssen et al. |
| 7,581,540 B2 | 9/2009 | Hale et al. |
| 7,597,099 B2 | 10/2009 | Jones et al. |
| 7,631,643 B2 | 12/2009 | Morrison et al. |
| 7,670,329 B2 | 3/2010 | Flaherty et al. |
| 7,672,726 B2 | 3/2010 | Ginggen |
| 7,677,467 B2 | 3/2010 | Fink et al. |
| 7,686,788 B2 | 3/2010 | Freyman et al. |
| 7,699,060 B2 | 4/2010 | Behm |
| 7,699,829 B2 | 4/2010 | Harris et al. |
| 7,708,011 B2 | 5/2010 | Hochrainer et al. |
| 7,713,229 B2 | 5/2010 | Veit et al. |
| 7,715,919 B2 | 5/2010 | Osorio et al. |
| 7,717,877 B2 | 5/2010 | Lavi et al. |
| 7,725,161 B2 | 5/2010 | Karmarkar et al. |
| 7,783,344 B2 | 8/2010 | Lackey et al. |
| 2001/0000802 A1 | 5/2001 | Soykan et al. |
| 2001/0022279 A1 | 9/2001 | Denyer et al. |
| 2002/0000225 A1 | 1/2002 | Schuler et al. |
| 2002/0002349 A1 | 1/2002 | Flaherty et al. |
| 2002/0010432 A1 | 1/2002 | Klitmose et al. |
| 2002/0013615 A1 | 1/2002 | Haim et al. |
| 2002/0026940 A1 | 3/2002 | Brooker et al. |
| 2002/0077852 A1 | 6/2002 | Ford et al. |
| 2002/0099328 A1 | 7/2002 | Scheiner et al. |
| 2002/0120236 A1 | 8/2002 | Diaz et al. |
| 2002/0153006 A1 | 10/2002 | Zimlich et al. |
| 2002/0189612 A1 | 12/2002 | Rand et al. |
| 2002/0189615 A1 | 12/2002 | Henry et al. |
| 2002/0198493 A1 | 12/2002 | Diaz et al. |
| 2003/0004236 A1 | 1/2003 | Meade et al. |
| 2003/0078561 A1 | 4/2003 | Gambale et al. |
| 2003/0079744 A1 | 5/2003 | Bonney et al. |
| 2003/0094508 A1 | 5/2003 | Peng et al. |
| 2003/0136418 A1 | 7/2003 | Behm et al. |
| 2003/0140921 A1 | 7/2003 | Smith et al. |
| 2003/0150446 A1 | 8/2003 | Patel et al. |
| 2003/0159693 A1 | 8/2003 | Melker et al. |
| 2003/0168057 A1 | 9/2003 | Snyder et al. |
| 2003/0171738 A1 | 9/2003 | Konieczynski et al. |
| 2003/0176804 A1 | 9/2003 | Melker et al. |
| 2003/0183226 A1 | 10/2003 | Brand et al. |
| 2003/0205229 A1 | 11/2003 | Crockford et al. |
| 2004/0004133 A1 | 1/2004 | Ivri et al. |

| | | |
|---|---|---|
| 2004/0019321 A1 | 1/2004 | Sage et al. |
| 2004/0025871 A1 | 2/2004 | Davies et al. |
| 2004/0031331 A1 | 2/2004 | Blakely et al. |
| 2004/0050385 A1 | 3/2004 | Bonney et al. |
| 2004/0089299 A1 | 5/2004 | Bonney et al. |
| 2004/0098117 A1 | 5/2004 | Hossainy et al. |
| 2004/0106902 A1 | 6/2004 | Diaz et al. |
| 2004/0122530 A1 | 6/2004 | Hansen et al. |
| 2004/0133154 A1 | 7/2004 | Flaherty et al. |
| 2004/0139963 A1 | 7/2004 | Ivri et al. |
| 2004/0158167 A1 | 8/2004 | Smith et al. |
| 2004/0181196 A1 | 9/2004 | Pickup et al. |
| 2004/0187864 A1 | 9/2004 | Adams et al. |
| 2004/0210199 A1 | 10/2004 | Atterbury et al. |
| 2004/0254435 A1 | 12/2004 | Mathews et al. |
| 2005/0010166 A1 | 1/2005 | Hickle |
| 2005/0045734 A1 | 3/2005 | Peng et al. |
| 2005/0059924 A1 | 3/2005 | Katz et al. |
| 2005/0072421 A1 | 4/2005 | Suman et al. |
| 2005/0081845 A1 | 4/2005 | Barney et al. |
| 2005/0087189 A1 | 4/2005 | Crockford et al. |
| 2005/0137626 A1 | 6/2005 | Pastore et al. |
| 2005/0139651 A1 | 6/2005 | Lim |
| 2005/0155602 A1 | 7/2005 | Lipp |
| 2005/0165342 A1 | 7/2005 | Odland |
| 2005/0172956 A1 | 8/2005 | Childers et al. |
| 2005/0172958 A1 | 8/2005 | Singer et al. |
| 2005/0183725 A1 | 8/2005 | Gumaste et al. |
| 2005/0203637 A1 | 9/2005 | Edman et al. |
| 2005/0235732 A1 | 10/2005 | Rush |
| 2005/0236501 A1 | 10/2005 | Zimlich et al. |
| 2005/0245906 A1 | 11/2005 | Makower et al. |
| 2005/0247312 A1 | 11/2005 | Davies |
| 2005/0251289 A1 | 11/2005 | Bonney et al. |
| 2005/0274378 A1 | 12/2005 | Bonney et al. |
| 2006/0030813 A1 | 2/2006 | Chance |
| 2006/0031099 A1 | 2/2006 | Vitello et al. |
| 2006/0037612 A1 | 2/2006 | Herder et al. |
| 2006/0042632 A1 | 3/2006 | Bishop et al. |
| 2006/0058593 A1 | 3/2006 | Drinan et al. |
| 2006/0090752 A1 | 5/2006 | Imondi et al. |
| 2006/0130832 A1 | 6/2006 | Schechter et al. |
| 2006/0131350 A1 | 6/2006 | Schechter et al. |
| 2006/0167530 A1 | 7/2006 | Flaherty et al. |
| 2006/0178586 A1 | 8/2006 | Dobak |
| 2006/0184087 A1 | 8/2006 | Wariar et al. |
| 2006/0191534 A1 | 8/2006 | Hickey et al. |
| 2006/0201499 A1 | 9/2006 | Muellinger et al. |
| 2006/0204532 A1 | 9/2006 | John |
| 2006/0231093 A1 | 10/2006 | Burge et al. |
| 2006/0243277 A1 | 11/2006 | Denyer et al. |
| 2006/0253005 A1 | 11/2006 | Drinan |
| 2006/0283465 A1 | 12/2006 | Nickel |
| 2007/0023034 A1 | 2/2007 | Jongejan et al. |
| 2007/0023036 A1 | 2/2007 | Grychowski et al. |
| 2007/0043591 A1 | 2/2007 | Meretei et al. |
| 2007/0044793 A1 | 3/2007 | Kleinstreuer et al. |
| 2007/0060800 A1 | 3/2007 | Drinan et al. |
| 2007/0074722 A1 | 4/2007 | Giroux et al. |
| 2007/0088334 A1 | 4/2007 | Hillis et al. |
| 2007/0091273 A1 | 4/2007 | Sullivan et al. |
| 2007/0123829 A1 | 5/2007 | Atterbury et al. |
| 2007/0125370 A1 | 6/2007 | Denyer et al. |
| 2007/0157931 A1 | 7/2007 | Parker et al. |
| 2007/0161879 A1 | 7/2007 | Say et al. |
| 2007/0169778 A1 | 7/2007 | Smith et al. |
| 2007/0197954 A1 | 8/2007 | Keenan |
| 2007/0203411 A1 | 8/2007 | Say et al. |
| 2007/0208322 A1 | 9/2007 | Rantala et al. |
| 2007/0209659 A1 | 9/2007 | Ivri et al. |
| 2007/0213658 A1 | 9/2007 | Hickle |
| 2007/0221218 A1 | 9/2007 | Warden et al. |
| 2007/0224128 A1 | 9/2007 | Dennis et al. |
| 2007/0240712 A1 | 10/2007 | Fleming et al. |
| 2007/0256688 A1 | 11/2007 | Schuster et al. |
| 2007/0258894 A1 | 11/2007 | Melker et al. |
| 2007/0295329 A1 | 12/2007 | Lieberman et al. |
| 2007/0299550 A1 | 12/2007 | Nishijima et al. |
| 2008/0009800 A1 | 1/2008 | Nickel |
| 2008/0021379 A1 | 1/2008 | Hickle |
| 2008/0039700 A1 | 2/2008 | Drinan et al. |
| 2008/0051667 A1 | 2/2008 | Goldreich |
| 2008/0058703 A1 | 3/2008 | Subramony et al. |
| 2008/0077080 A1 | 3/2008 | Hengstenberg et al. |
| 2008/0078382 A1 | 4/2008 | LeMahieu et al. |
| 2008/0078385 A1 | 4/2008 | Xiao et al. |
| 2008/0082001 A1 | 4/2008 | Hatlestad et al. |
| 2008/0086112 A1 | 4/2008 | Lo et al. |
| 2008/0091138 A1 | 4/2008 | Pastore et al. |
| 2008/0114299 A1 | 5/2008 | Damgaard-Sorensen et al. |
| 2008/0125759 A1 | 5/2008 | Konieczynski et al. |
| 2008/0142002 A1 | 6/2008 | Fink et al. |
| 2008/0147004 A1 | 6/2008 | Mann et al. |
| 2008/0147050 A1 | 6/2008 | Mann et al. |
| 2008/0173301 A1 | 7/2008 | Deaton et al. |
| 2008/0177246 A1 | 7/2008 | Sullican et al. |
| 2008/0178872 A1 | 7/2008 | Genova et al. |
| 2008/0200804 A1 | 8/2008 | Hartlep et al. |
| 2008/0216834 A1 | 9/2008 | Easley et al. |
| 2008/0221408 A1 | 9/2008 | Hoarau et al. |
| 2008/0262469 A1 | 10/2008 | Brister et al. |
| 2008/0269689 A1 | 10/2008 | Edwards et al. |
| 2008/0281276 A1 | 11/2008 | Shekalim |
| 2008/0306436 A1 | 12/2008 | Edwards et al. |
| 2008/0306444 A1 | 12/2008 | Brister et al. |
| 2008/0306449 A1 | 12/2008 | Kristensen et al. |
| 2009/0005763 A1 | 1/2009 | Makower et al. |
| 2009/0024112 A1 | 1/2009 | Edwards et al. |
| 2009/0025714 A1 | 1/2009 | Denyer et al. |
| 2009/0025718 A1 | 1/2009 | Denyer et al. |
| 2009/0048526 A1 | 2/2009 | Aarts et al. |
| 2009/0048556 A1 | 2/2009 | Durand |
| 2009/0056708 A1 | 3/2009 | Stenzler |
| 2009/0064997 A1 | 3/2009 | Li |
| 2009/0082829 A1 | 3/2009 | Panken et al. |
| 2009/0107503 A1 | 4/2009 | Baran |
| 2009/0151718 A1 | 6/2009 | Hunter et al. |
| 2009/0156952 A1 | 6/2009 | Hunter et al. |
| 2009/0163781 A1 | 6/2009 | Say et al. |
| 2009/0187167 A1 | 7/2009 | Sexton et al. |
| 2009/0194104 A1 | 8/2009 | Van Sickle |
| 2009/0211576 A1 | 8/2009 | Lehtonen et al. |
| 2009/0213373 A1 | 8/2009 | Altobelli et al. |
| 2009/0216194 A1 | 8/2009 | Elgard et al. |
| 2009/0221087 A1 | 9/2009 | Martin et al. |
| 2009/0227941 A1 | 9/2009 | Say et al. |
| 2009/0229607 A1 | 9/2009 | Brunnberg et al. |
| 2009/0241951 A1 | 10/2009 | Jafari et al. |
| 2009/0241955 A1 | 10/2009 | Jafari et al. |
| 2009/0270752 A1 | 10/2009 | Coifman |
| 2009/0301472 A1 | 12/2009 | Kim et al. |
| 2009/0314372 A1 | 12/2009 | Ruskewicz et al. |
| 2009/0326509 A1 | 12/2009 | Muse et al. |
| 2009/0326510 A1 | 12/2009 | Haefner et al. |
| 2010/0012120 A1 | 1/2010 | Herder et al. |
| 2010/0031957 A1 | 2/2010 | McIntosh |
| 2010/0049004 A1 | 2/2010 | Edman et al. |
| 2010/0049172 A1 | 2/2010 | Chance |
| 2010/0078015 A1 | 4/2010 | Imran |
| 2010/0094099 A1 | 4/2010 | Levy et al. |
| 2010/0099967 A1 | 4/2010 | Say et al. |
| 2010/0100078 A1 | 4/2010 | Say et al. |
| 2010/0100160 A1 | 4/2010 | Edman et al. |
| 2010/0106098 A1 | 4/2010 | Alterbury et al. |
| 2010/0114026 A1 | 5/2010 | Karratt et al. |
| 2010/0114060 A1 | 5/2010 | Ginggen et al. |
| 2010/0116070 A1 | 5/2010 | Farina et al. |
| 2010/0121314 A1 | 5/2010 | Iobbi |
| 2010/0122697 A1 | 5/2010 | Przekwas et al. |
| 2010/0268111 A1 | 10/2010 | Drinan et al. |
| 2011/0224912 A1 | 9/2011 | Bhavaraju et al. |
| 2011/0230732 A1 | 9/2011 | Edman et al. |

FOREIGN PATENT DOCUMENTS

| | | |
|---|---|---|
| JP | 2001-061799 | 3/2001 |
| JP | 2008-525063 | 7/2008 |
| WO | WO8102982 | 10/1981 |
| WO | WO8607269 | 12/1986 |

| | | | | | |
|---|---|---|---|---|---|
| WO | WO9207599 | 5/1992 | WO | WO02089884 | 11/2002 |
| WO | WO9209324 | 6/1992 | WO | WO02096489 | 12/2002 |
| WO | WO9211808 | 7/1992 | WO | WO03006091 | 1/2003 |
| WO | WO9215353 | 9/1992 | WO | WO03008014 | 1/2003 |
| WO | WO9217231 | 10/1992 | WO | WO03020349 | 3/2003 |
| WO | WO9306803 | 4/1993 | WO | WO03022327 | 3/2003 |
| WO | WO9312823 | 7/1993 | WO | WO03028797 | 4/2003 |
| WO | WO9405359 | 3/1994 | WO | WO03035172 | 5/2003 |
| WO | WO9408655 | 4/1994 | WO | WO03038566 | 5/2003 |
| WO | WO9416755 | 8/1994 | WO | WO03045302 | 6/2003 |
| WO | WO9416756 | 8/1994 | WO | WO03059413 | 7/2003 |
| WO | WO9416759 | 8/1994 | WO | WO03071930 | 9/2003 |
| WO | WO9427653 | 12/1994 | WO | WO03073977 | 9/2003 |
| WO | WO9507723 | 3/1995 | WO | WO03086505 | 10/2003 |
| WO | WO9507724 | 3/1995 | WO | WO03090821 | 11/2003 |
| WO | WO9513838 | 5/1995 | WO | WO03097120 | 11/2003 |
| WO | WO9526769 | 10/1995 | WO | WO2004009161 | 1/2004 |
| WO | WO9610440 | 4/1996 | WO | WO2004011067 | 2/2004 |
| WO | WO9616686 | 6/1996 | WO | WO2004012801 | 2/2004 |
| WO | WO9625186 | 8/1996 | WO | WO2004020024 | 3/2004 |
| WO | WO9625978 | 8/1996 | WO | WO2004021882 | 3/2004 |
| WO | WO9627341 | 9/1996 | WO | WO2004022128 | 3/2004 |
| WO | WO9630078 | 10/1996 | WO | WO2004022153 | 3/2004 |
| WO | WO9707896 | 3/1997 | WO | WO2004022242 | 3/2004 |
| WO | WO9711655 | 4/1997 | WO | WO2004026380 | 4/2004 |
| WO | WO9711742 | 4/1997 | WO | WO2004032989 | 4/2004 |
| WO | WO9711743 | 4/1997 | WO | WO2004034998 | 4/2004 |
| WO | WO9726934 | 7/1997 | WO | WO2004041334 | 5/2004 |
| WO | WO9733640 | 9/1997 | WO | WO2004041339 | 5/2004 |
| WO | WO9733645 | 9/1997 | WO | WO2004045690 | 6/2004 |
| WO | WO9748431 | 12/1997 | WO | WO2004060436 | 7/2004 |
| WO | WO9800188 | 1/1998 | WO | WO2004060443 | 7/2004 |
| WO | WO9801168 | 1/1998 | WO | WO2004060447 | 7/2004 |
| WO | WO9806450 | 2/1998 | WO | WO2004080522 | 9/2004 |
| WO | WO9814235 | 4/1998 | WO | WO2004088567 | 10/2004 |
| WO | WO9832479 | 7/1998 | WO | WO2005009514 | 2/2005 |
| WO | WO9839057 | 9/1998 | WO | WO2005011779 | 2/2005 |
| WO | WO9844984 | 10/1998 | WO | WO2005028008 | 3/2005 |
| WO | WO9850095 | 11/1998 | WO | WO2005031317 | 4/2005 |
| WO | WO9900144 | 1/1999 | WO | WO2005039750 | 5/2005 |
| WO | WO9930760 | 6/1999 | WO | WO2005046559 | 5/2005 |
| WO | WO9965551 | 12/1999 | WO | WO2005051177 | 6/2005 |
| WO | WO0001434 | 1/2000 | WO | WO2005072798 | 8/2005 |
| WO | WO0007652 | 2/2000 | WO | WO2005084275 | 9/2005 |
| WO | WO0018339 | 4/2000 | WO | WO2005084738 | 9/2005 |
| WO | WO0021598 | 4/2000 | WO | WO2005087299 | 9/2005 |
| WO | WO0027278 | 5/2000 | WO | WO2005102412 | 11/2005 |
| WO | WO0032267 | 6/2000 | WO | WO2005102417 | 11/2005 |
| WO | WO0038770 | 7/2000 | WO | WO2005102418 | 11/2005 |
| WO | WO0043059 | 7/2000 | WO | WO2005102428 | 11/2005 |
| WO | WO0047253 | 8/2000 | WO | WO2005120615 | 12/2005 |
| WO | WO0050111 | 8/2000 | WO | WO2005123002 | 12/2005 |
| WO | WO0053247 | 9/2000 | WO | WO2006003665 | 1/2006 |
| WO | WO0059483 | 10/2000 | WO | WO2006009596 | 1/2006 |
| WO | WO0105463 | 1/2001 | WO | WO2006015299 | 2/2006 |
| WO | WO0113973 | 3/2001 | WO | WO2006022714 | 3/2006 |
| WO | WO0124851 | 4/2001 | WO | WO2006023644 | 3/2006 |
| WO | WO0130419 | 5/2001 | WO | WO2006029090 | 3/2006 |
| WO | WO0158236 | 8/2001 | WO | WO2006035443 | 4/2006 |
| WO | WO0168169 | 9/2001 | WO | WO2006044206 | 4/2006 |
| WO | WO0183007 | 11/2001 | WO | WO2006045524 | 5/2006 |
| WO | WO0185027 | 11/2001 | WO | WO2006058426 | 6/2006 |
| WO | WO0187378 | 11/2001 | WO | WO2006060106 | 6/2006 |
| WO | WO0189607 | 11/2001 | WO | WO2006069323 | 6/2006 |
| WO | WO0200280 | 1/2002 | WO | WO2006079898 | 8/2006 |
| WO | WO0202052 | 1/2002 | WO | WO2006096286 | 9/2006 |
| WO | WO0204043 | 1/2002 | WO | WO2006098933 | 9/2006 |
| WO | WO0217988 | 3/2002 | WO | WO2006098936 | 9/2006 |
| WO | WO0217998 | 3/2002 | WO | WO2006113408 | 10/2006 |
| WO | WO0224257 | 3/2002 | WO | WO2006116718 | 11/2006 |
| WO | WO0224268 | 3/2002 | WO | WO2006120253 | 11/2006 |
| WO | WO0234318 | 5/2002 | WO | WO2006124759 | 11/2006 |
| WO | WO0236181 | 5/2002 | WO | WO2006125577 | 11/2006 |
| WO | WO02053223 | 7/2002 | WO | WO2006127257 | 11/2006 |
| WO | WO02072178 | 9/2002 | WO | WO2006127905 | 11/2006 |
| WO | WO02076533 | 10/2002 | WO | WO2006127953 | 11/2006 |
| WO | WO02078535 | 10/2002 | WO | WO2006128794 | 12/2006 |
| WO | WO02081016 | 10/2002 | WO | WO2006130098 | 12/2006 |
| WO | WO02089879 | 11/2002 | WO | WO2006133101 | 12/2006 |

| | | |
|---|---|---|
| WO | WO2007012854 | 2/2007 |
| WO | WO2007028035 | 3/2007 |
| WO | WO2007031740 | 3/2007 |
| WO | WO2007034237 | 3/2007 |
| WO | WO2007041158 | 4/2007 |
| WO | WO2007041471 | 4/2007 |
| WO | WO2007051563 | 5/2007 |
| WO | WO2007070093 | 6/2007 |
| WO | WO2007070695 | 6/2007 |
| WO | WO2007120884 | 10/2007 |
| WO | WO2007125699 | 11/2007 |
| WO | WO2007127981 | 11/2007 |
| WO | WO2007131025 | 11/2007 |
| WO | WO2008016698 | 2/2008 |
| WO | WO2008021252 | 2/2008 |
| WO | WO2008022010 | 2/2008 |
| WO | WO2008029403 | 3/2008 |
| WO | WO2008030837 | 3/2008 |
| WO | WO2008037801 | 4/2008 |
| WO | WO2008038241 | 4/2008 |
| WO | WO2008039091 | 4/2008 |
| WO | WO2008043724 | 4/2008 |
| WO | WO2008052039 | 5/2008 |
| WO | WO2008073806 | 6/2008 |
| WO | WO2008077706 | 7/2008 |
| WO | WO2008078287 | 7/2008 |
| WO | WO2008095183 | 8/2008 |
| WO | WO2008103620 | 8/2008 |
| WO | WO2008115906 | 9/2008 |
| WO | WO2008117226 | 10/2008 |
| WO | WO2008127743 | 10/2008 |
| WO | WO2008130801 | 10/2008 |
| WO | WO2008134107 | 11/2008 |
| WO | WO2008134545 | 11/2008 |
| WO | WO2008152588 | 12/2008 |
| WO | WO2008154312 | 12/2008 |
| WO | WO2008154504 | 12/2008 |
| WO | WO2009003989 | 1/2009 |
| WO | WO2009008001 | 1/2009 |
| WO | WO2009013501 | 1/2009 |
| WO | WO2009013670 | 1/2009 |
| WO | WO2009023247 | 2/2009 |
| WO | WO2009035759 | 3/2009 |
| WO | WO2009042379 | 4/2009 |
| WO | WO2009049252 | 4/2009 |
| WO | WO2009063421 | 5/2009 |
| WO | WO2009072079 | 6/2009 |
| WO | WO2009076363 | 6/2009 |
| WO | WO2009079589 | 6/2009 |
| WO | WO2009081262 | 7/2009 |
| WO | WO2009091851 | 7/2009 |
| WO | WO2009098648 | 8/2009 |
| WO | WO2009105337 | 8/2009 |
| WO | WO2009126653 | 10/2009 |
| WO | WO2009137661 | 11/2009 |
| WO | WO2009140251 | 11/2009 |
| WO | WO2009145801 | 12/2009 |
| WO | WO2009155335 | 12/2009 |
| WO | WO2010007573 | 1/2010 |
| WO | WO2010007574 | 1/2010 |
| WO | WO2010008424 | 1/2010 |
| WO | WO2010010473 | 1/2010 |
| WO | WO2010021589 | 2/2010 |
| WO | WO2010023591 | 3/2010 |
| WO | WO2010025428 | 3/2010 |
| WO | WO2010025431 | 3/2010 |
| WO | WO2010029054 | 3/2010 |
| WO | WO2010037828 | 4/2010 |
| WO | WO2010042034 | 4/2010 |
| WO | WO2010043054 | 4/2010 |
| WO | WO2010045460 | 4/2010 |
| WO | WO2010051551 | 5/2010 |
| WO | WO2010052275 | 5/2010 |
| WO | WO2010062675 | 6/2010 |

OTHER PUBLICATIONS

Nikander et al., "The Adaptive Delivery System in a Telehealth Setting: Patient Acceptance, Performance and Feasibility" Journal of Aerosol Medicine and Pulmonary Drug Delivery; vol. 23, Supp. 1, (2010) pp. S21-S27.
Juvenile Diabetes Research Foundation International (JDRF), "Artificial Pancreas Project" (2010); http://www.artificialpancreasproject.com/; 3 pp.
LIFESCAN, "OneTouch UltraLink™" http://www.lifescan.com/products/meters/ultralink (N.D.) 2 pp., Jul. 2010.
MEDTRONIC, "CareLink Therapy Management Software for Diabetes" (2010); https://carelink.minimed.com/patient/entry.jsp?bhcp=1; 1 pp.
MEDTRONIC, "Carelink™ USB" (n.d.) http://www.medtronicdiabetes.com/pdf/carelink_usb_factsheet.pdf 2pp., 2010.
MEDTRONIC, "The New MiniMed Paradigm® REAL-Time Revel™ System" http://www.medtronicdiabetes.com/products/index.html; 2 pp.
MEDTRONIC, "MINI MED Paradigm® Revel™ Insulin Pump" (n.d.) http://www.medtronicdiabetes.com/products/insulinpumps/index.html; 2 pp., 2010.
MEDTRONIC, Mini Med Paradigm™ Veo™ System: Factsheet (2010), http://www.medtronic-diabetes.com.au/downloads/Paradigm%20Veo%20Factsheet.pdf ; 4 pp.
Park, "Medtronic to Buy MiniMed for $3.7 Billion" (2001) HomeCare; http://homecaremag.com/mag/medical_medtronic_buy_minimed/; 2 pp.
Prutchi et al., "Design and Development of Medical Electronic Instrumentation: A Practical Perspective of the Design, Construction, and Test of Medical Devices" Wiley-Interscience (2005) pp. 12-14.

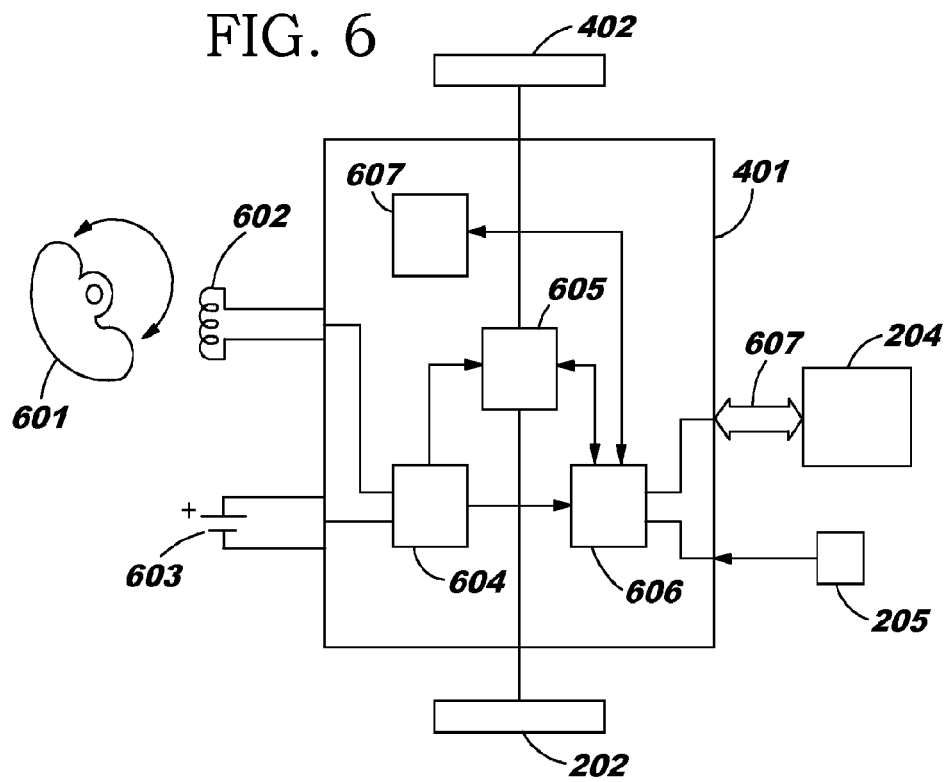
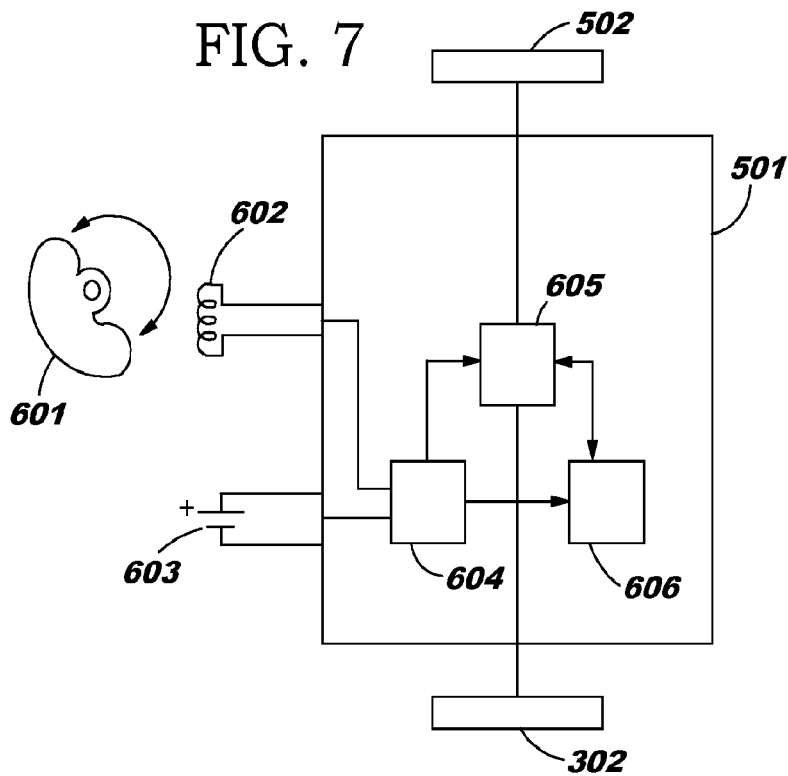

TWO-WRIST DATA GATHERING SYSTEM

CROSS-REFERENCE TO RELATED APPLICATION

This application claims priority pursuant to 35 U.S.C. §119 to U.S. application Ser. No. 61/300,435 filed Feb. 1, 2010, and entitled "Two-wrist data-gathering system". The foregoing is incorporated by reference in its entirety.

INTRODUCTION

It is not easy to know whether a patient has taken his or her medication.

The assignee of the present invention has given much attention in recent years to ways of detecting ingestion of medications such as pills. Through great effort, the assignee of the present invention has devised systems involving pills each containing a device with communication means, e.g., conductive communication means, etc., and involving a receiver such as a patch applied to the skin of a patient, so that when one of the pills reaches the stomach, gastric acids activate the device which communicates a current signature. The patch picks up the current signature, thus detecting the ingestion of the pill. The patch can then pass along this event to other equipment and systems. For example the patch may use a Bluetooth protocol to send news of the event to a mobile telephone, which in turn can pass the event to other equipment. A typical patch location is the abdomen.

While the assignee of the present invention has had good results in its systems that use a patch in this way, the patch is sometimes inconvenient. It may be uncomfortable. It needs to be able to be flexible, since it adheres to skin that flexes. It is not easy to provide much of a man-machine interface ("MMI") on a patch located at the abdomen. Keyboards and displays are not very workable if they are on a planar surface adhered to the abdomen.

An abdominal patch has a power source, typically a battery or electrochemical cell (here for convenience of reference we will use the term "cell" to refer both to multicell batteries and to single cells). The cell has only a limited service life, defined in large part by the capacity of the cell and by the energy budget of the patch. When the battery is run down, the patch needs to be taken out of service and a different patch needs to be put into service. This can also be inconvenient.

When the pill gets triggered, it emits a signal, sends a communication, etc. . . . An exemplary pill and communication are described in detail in, for example, in the following US patent publications:

| U.S. Publication No. | Publication date | Title |
| --- | --- | --- |
| 2008/0,284,599 | Nov. 20, 2008 | Pharma-informatics system |
| 2008/0,306,359 | Dec. 11, 2008 | Medical diagnostic and treatment platform using near-field wireless communication of information within a patient's body |
| 2009/0,082,645 | Mar. 26, 2009 | In-body device with virtual dipole signal amplification |
| 2009/0,227,204 | Sep. 10, 2009 | Pharma-informatics system |
| 2010/0,022,836 | Jan. 28, 2010 | In-body device having a multi-directional transmitter |
| 2010/0,081,894 | Apr. 1, 2010 | Communication System with Partial Power Source |
| 2010/0,312,188 | Dec. 9, 2010 | Pharma-informatics system | each of which is incorporated herein by reference for all purposes as if reproduced fully within. Actual tests with real pills, real patches, and real human subjects have achieved reliable detection of communications from such pills. This is remarkable given prior-art failures to achieve such reliable detection, and the many ways in which nature, human physiology, and materials science conspire to make these results difficult to achieve.

As a general matter, conventional electromagnetic radiation is emitted by a dipole and detected and received by a dipole, and conventional models assume that the signal strength falls away with distance at a rate determined by the permittivity and permeability of the medium (here, human tissue). Many investigators in this general area thus proceed with the assumption that the receiver, such as a patch, needs to be as nearby as possible to the transmitter (that is, nearby to the stomach).

It would be very desirable if some way could be found to detect the triggering of the pill transmitters that would avoid the inconveniences related to patches as just described, while nonetheless achieving the reliable detection that has been accomplished using patches. There are other physiological measurements that would also be desirable to carry out if only it could be accomplished reliably and accurately without undue discomfort or inconvenience to the patient.

SUMMARY

It is very counter-intuitive to carry out sensing from locations at considerable remove from the stomach, given that in general one might think the receiver needs to be as close as possible to the transmitter. And yet that is precisely what is described here. Cooperating sensor electronics are placed at each of two wrists of the patient. Once the counter-intuitive nature of this arrangement is put out of mind, other potential benefits become readily available, for example a man-machine interface can be provided. The potential discomfort and inconvenience of an abdominal patch are reduced or eliminated. And alternative power sources become available.

DESCRIPTION OF THE DRAWING

The invention is described with respect to a drawing in several figures, of which:

FIG. 6 shows chip 401 in functional block diagram form; and

FIG. 7 shows chip 501 in functional block diagram form.

To the extent possible, like elements have been denoted with like reference numerals.

DETAILED DESCRIPTION

Figure 1:
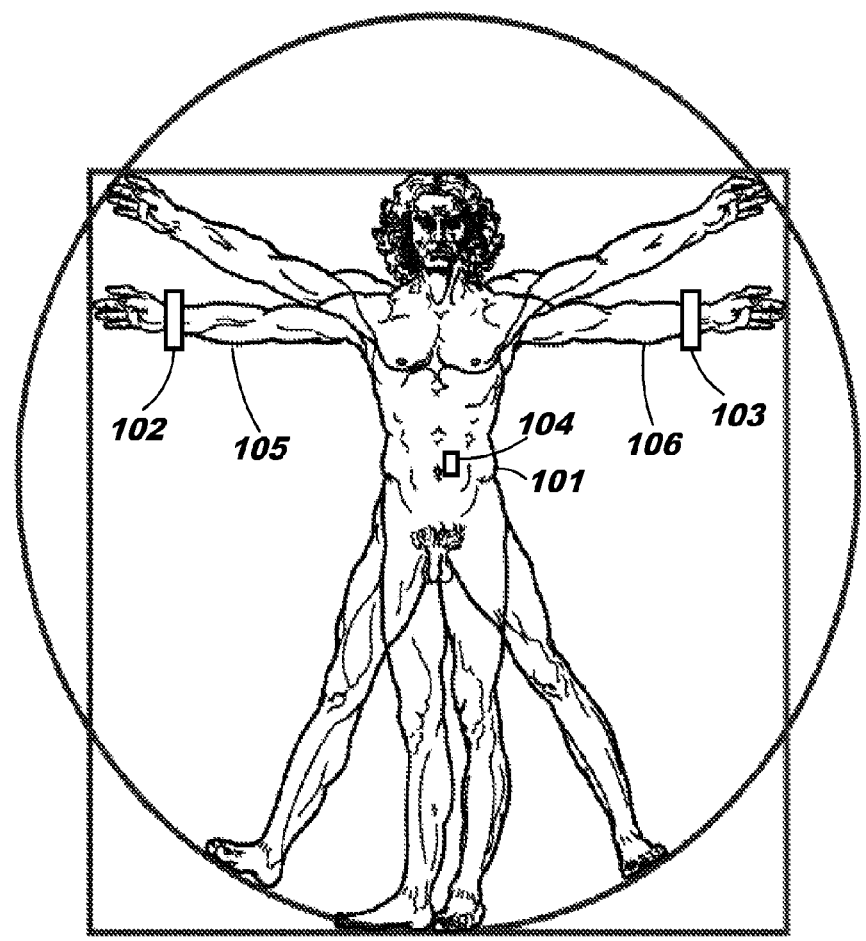
FIG. 1 shows a patient 101 with a wristwatch 102 and a bracelet 103 according to an aspect of the invention.

FIG. 1 shows a patient 101 with a wristwatch 102 and a bracelet 103 according to an aspect of the invention. Wristwatch 102 is on right wrist 105 and bracelet 103 is on left wrist 106. (It will be appreciated that this left-right arrangement is quite arbitrary and one could exchange the positions of the wristwatch and bracelet without departing from the invention.) One of the chief goals is to detect a transmitted signal or communication from pill 104 when it is triggered by gastric juices.

It will be appreciated that while this invention is described in an exemplary aspect where stomach juices trigger the pill, other variants could be devised such as aspects where the triggering does not occur until the pill reaches, say, the small intestine. One could also devise a staged approach where a first signal is triggered at a first point of progress through the gastro-intestinal system and a second signal is triggered at a second point of progress.

Figure 2:
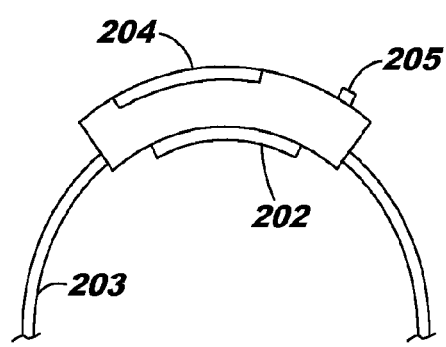
FIG. 2 shows the wristwatch 102 with elastic band 203.

Turning now to FIG. 2, we see an exemplary wristwatch 102 with elastic band 203. The elastic band helps to keep the electrode 202 in intimate contact with skin of the patient. A display 204, such as an LCD, is shown. A pushbutton 205 is also shown. In this way a man-machine interface (MMI) is provided. It will be appreciated, of course, that the MMI need not be limited to what is shown here. Other elements of an MMI, such as a piezo beeper or other sound source, could be provided. A touch screen or other human input device (HID) could be used. The LCD and pushbutton are merely exemplary.

While this aspect is described with respect to elastic wristbands, other approaches such as a Speidel Twist-o-flex® watchband could be employed to keep each skin electrode in intimate contact with the skin.

Figure 3:
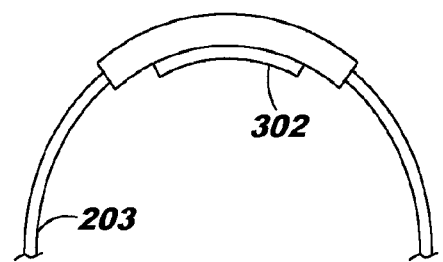
FIG. 3 shows the bracelet 103 with elastic band 203.

FIG. 3 shows the bracelet 103 with elastic band 203. The elastic band keeps electrode 302 in intimate contact with skin of the patient.

In the exemplary arrangements that follow, the electrodes 202, 302 will be described as electrodes in intimate (conductive) contact with skin. Perhaps less preferred, but also workable, would be electrodes 202, 302 in capacitive coupling with skin, that is, with some dielectric such as plastic film therebetween. Perhaps even less preferred, but maybe also workable, would be an arrangement in which the wristband 203 is not elastic at all but is of constant circumference, permitting the electrodes 202, 302 to be in a spaced relationship relative to skin, sometimes having an air gap or partial air gap therebetween.

Figure 4:
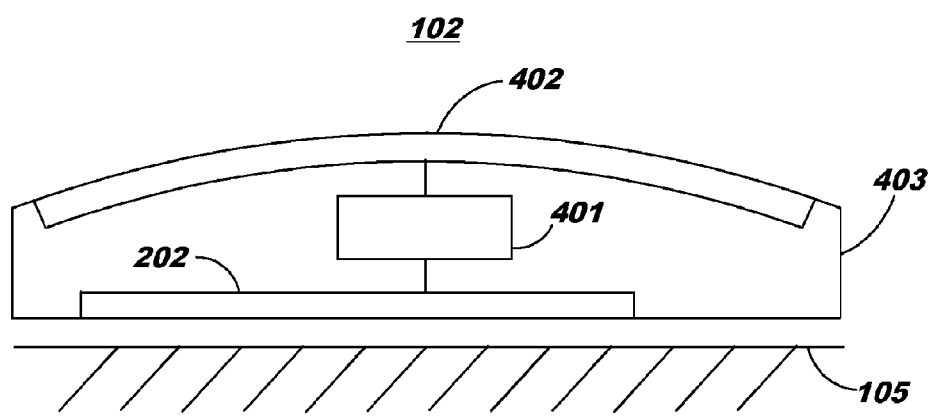
FIG. 4 shows the wristwatch 102 in cross section, with electrode 202 in intimate juxtaposition with wrist 105, and with chip 401.
Figure 5:
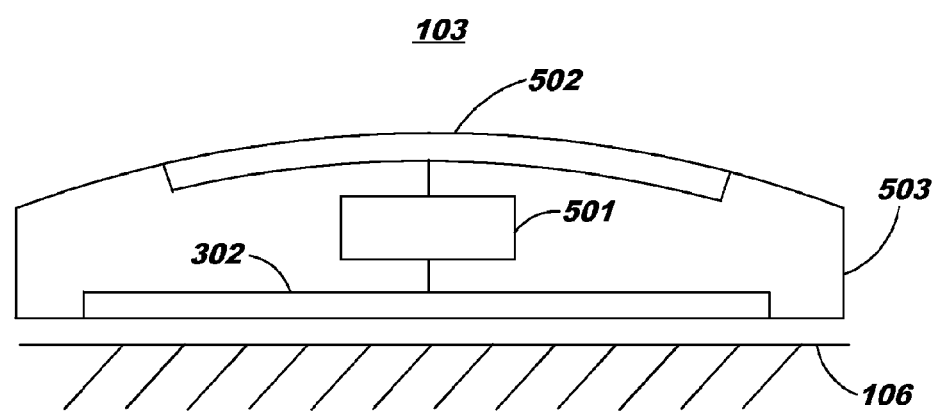
FIG. 5 shows the bracelet 103 in cross section, with electrode 302 in intimate juxtaposition with wrist 106, and with chip 501.

FIG. 4 shows the wristwatch 102 in cross section, with electrode 202 in intimate juxtaposition with wrist 105, and with chip 401. Chip 401 is communicatively coupled, preferably metallically connected, with skin electrode 202 and with a second electrode 402. The second electrode 402 is open to the air, and provides what might be modeled as a counterpoise for the skin electrode 202. A nonconductive casing 403 provides structure between the two electrodes. FIG. 5 shows the bracelet 103 in cross section, with electrode 302 in intimate juxtaposition with wrist 106, and with chip 501 in communicative coupling with skin electrode 302 and second electrode 502. The bracelet electrodes together with housing or casing 503 function similarly to their counterparts in the wristwatch.

FIG. 6 shows wristwatch chip 401 in functional block diagram form. Previously mentioned electrodes 202, 402 may be seen, communicatively coupled with transceiver 605. Cell 603 and power circuitry 604 provide power to transceiver 605 and to controller 606. Controller 606 controls transceiver 605 and provides MMI such as LCD 204 and pushbutton 205, and optionally other MMI such as a piezo beeper or other sound emitter. LCD 204 is controlled by multiline bus 607.

Interestingly, a technology that seems rather old-fashioned, the self-winding mechanical watch, offers possible benefits here. As shown in FIG. 6, a pendulum 601 has an opportunity to move around as the human user moves around. A strong permanent magnet in the pendulum induces currents in a winding or windings 602. This permits the cell 603 to be a rechargeable cell, or perhaps an ultracapacitor, mediated by power circuitry 604. Bluetooth or other protocol system(s) 607 can communicate with external equipment such as a cell phone or personal computer.

FIG. 7 shows bracelet chip 501 in functional block diagram form. The elements shown there correspond closely with elements in FIG. 6.

The day-to-day function of the system (the pills, the bracelet, the wristwatch, and other equipment such as a mobile phone) will now be described in an exemplary aspect.

A chief goal is to detect, at the bracelet 103 and wristwatch 102, a signal from a pill. To this end, the bracelet may carry out a real-time nearly continuous detection of signals at the skin electrode 302 relative to counterpoise 502. This detection is A-to-D (analog-to-digital) converted, e.g., by an ADC (not shown in FIG. 7), preferable at a resolution higher than 16 bits, and the measured signal (communicated digitally and preferably as compressed data) is communicated via a wireless link to the wristwatch 102. The wristwatch likewise carries out a real-time nearly continuous detection of signals at the skin electrode 202 relative to counterpoise 402. This detection is A-to-D (analog-to-digital) converted, preferable at a resolution higher than 16 bits. The data streams from the two sensors (one at the bracelet, one at the wristwatch) are then communicated externally to other equipment that can do signal processing and can detect signals of interest such as the signal from the pill when it is triggered.

In a preferred arrangement, all of the noise would be common-mode and the signals of interest would be differential signals measured at the two arms.

As mentioned above, it is rather counterintuitive to take the step of moving the sensors to points that are about as far from the pill 104 as can be imagined. Once the counterintuitive nature of this move is accepted and put out of mind, many other interesting capabilities become available that would likely not have been available at all in prior-art arrangements such as an abdominal patch.

Technology suitable for such sensing is discussed in a paper entitled "A low-noise, non-contact EEG/ECG sensor" by Thomas J Sullivan, Stephen R. Deiss, and Gert Gauwenberghs of the University of California, San Diego, Biomedical Circuits and Systems Conference, 2007, BIOCAS 2007, IEEE, 27-30 Nov. 2007 Pages 154-157, Digital Object Identifier 10.1109/BIOCAS.2007.4463332, incorporated herein by reference.

Sensing things from further away from the body is discussed in PCT publication WO 2009/055733 entitled "Fluid transfer port information system", incorporated herein by reference, and in US published application US 2009-0112178 A1 with the same title, likewise incorporated herein by reference. Sensing blood volume is discussed in U.S. patent application No. 61/160,265 filed Mar. 13, 2009 and entitled "Volume-sensing device, system, and method", incorporated herein by reference. Other related technology is discussed in US patent application No. 61/240,571 filed Sep. 8, 2009 and entitled "Body-associated device", incorporated herein by reference.

As one potential benefit mentioned above, the move to the wrists permits the provision of a workable MMI. Wrists also tend to move around more than abdomens, making the self-winding feature more likely to serve its purpose.

More subtle and interesting capabilities, however, present themselves once the stimulus/sensing platform of a bracelet and wristwatch are available.

The heart function (essentially a two-electrode EKG) can be measured.

Energy can be transmitted at one of the two points (for example at the bracelet) at some frequency, which propagates through the body to the other point (in this example at the wristwatch) with some measured delay and some measured level of absorption, or measured impedance. Separately, energy can be transmitted at one of the two points (again for example at the bracelet) at a different frequency, which propagates through the body to the other point (again in this example at the wristwatch) with a non-identical measured delay and a non-identical measured level of absorption, or measured impedance. This probing of the body amounts to spectroscopy, and permits measuring bodily qualities such as amount of fluid in the body relative to other tissue materials. In this way, blood volume can be indirectly measured. Real-time measurement of blood volume has rarely if ever been achieved except by keeping a patient stationary during measurements, with large, bulky, and stationary measuring equipment. This approach permits real-time measurement even as a patient is ambulatory.

These measurements may permit real-time measurement of cardiac output or stroke volume at the heart.

It will be appreciated that one of the important parts of analysis of data collected at electrodes 202, 302 (at the bracelet and at the watchband) is the time-correlation of measured data. One might think that this requires a highly accurate clock running in each of the bracelet and watchband, the two clocks being extremely closely synchronized.

But in fact it is quite workable to allow the two clocks to be less expensive (and less power-hungry) clocks that are permitted to drift relative to each other. At the wristwatch, synchronization events (simultaneous detection of common-mode impulse signals from the environment, for example) permit receiving a time signal from the bracelet which will then be understood to match a time value at the wristwatch. Drift of one clock relative to the other can be detected and corrected in this way.

The wristwatch and bracelet can be stylish. They need not look "clunky". The patient might actually enjoy wearing a recognizable or distinctive wristwatch and bracelet.

The A-to-D conversions at the two sensing locations are likely 18-bit, but might be sixteen-bit or twelve-bit.

Communication from the bracelet to the wristwatch might be open-loop (one way from bracelet to watchband) but it is thought preferable that the communication be bidirectional, at least to provide handshaking.

The communication may use an inductive coupling through the body at a high-frequency RF signal (higher than the sensed information that is expected to be in the range of 0.1 Hz to perhaps 100 Hz). Alternatively the communication can be optical infrared (bouncing off the surrounding walls and structures).

The MMI might provide a reminder to take a particular pill. And the MMI might provide an audible or visual acknowledgment when the patient has taken a particular pill.

Accelerometers in the bracelet or watchband or both will permit measurement of a physical activity level, and may permit detecting times of sleep. These could likewise be reported external to the patient.

The allocation of computational resources can be varied somewhat. For example it may be workable to do most of the computations in the wristwatch, comparing the signals as measured at the bracelet and at the wristwatch. Alternatively it is workable to do the computations elsewhere (e.g. at a distant computer) and to have the wristwatch simply pass along the information which it received from the bracelet.

The needed bandwidth from bracelet to wristwatch, and from wristwatch to distant equipment, is such at a carrier of 10 MHz should be adequate.

The alert reader will have no difficulty devising myriad obvious improvements and variants of the invention, all of which are intended to be encompassed by the claims which follow.

The invention claimed is:

1. A data gathering method carried out with respect to a first device and a second device, each of the first device and the second device comprising a respective electrical signal detector having respective first and second electrodes, the method comprising the steps of:
    placing a first device upon a first limb of a living body, the first device encircling said first limb, the first electrode of the first device juxtaposed with said first limb, the second electrode of the first device more distant from the first limb than the first electrode;
    placing a second device upon a second limb of a body, the second device encircling said second limb, the second limb being a limb other than the first limb, the first electrode of the first device juxtaposed with said second limb, the second electrode of the second device more distant from the second limb than the first electrode;
    at the first device, measuring electrical signals at the respective signal detector differentially between the respective first and second electrodes, yielding a first data stream indicative thereof;
    at the second device, measuring electrical signals at the respective signal detector differentially between the respective first and second electrodes, yielding a second data stream indicative thereof; and
    analyzing the first data stream and the second data stream together, thereby deriving information of interest about the body.

2. The method of claim 1 wherein the analyzing step further comprises synchronizing the first data stream to the second data stream by aligning common-mode events therein.

3. The method of claim 1 wherein the analyzing step is carried out at equipment separate from the first device and separate from the second device, the method further comprising the steps of:
    communicating the first data stream from the first device to the equipment, and
    communicating the second data stream from the second device to the equipment.

4. The method of claim 1 further characterized in that the first limb is a first arm of the body, and the second limb is a second arm of the body, and wherein the encircling of the first device comprises encircling a wrist of the first limb, and wherein the encircling of the second device comprises encircling a wrist of the second limb.

5. The method of claim 1 wherein the analyzing step comprises detecting at least one of a signal and a communication associated with an ingestible device ingested by the body.

6. The method of claim 1 wherein the first device has a rechargeable energy storage, the method further comprising the step of moving the first limb, and converting movement of the first limb into electrical energy, said electrical energy recharging the rechargeable energy storage.

7. The method of claim 6 further comprising the steps of:
    inferring a level of physical activity of the body from the converted electrical energy, and communicating the inferred level of physical activity external to the first device and external to the second device.

8. The method of claim 1 wherein the measuring of electrical signals at the first device comprises carrying out an analog-to-digital conversion, the first data stream being digital, and wherein the measuring of electrical signals at the second device comprises carrying out an analog-to-digital conversion, the second data stream being digital.

9. The method of claim 8 wherein the analog-to-digital conversions take place with a resolution of at least sixteen bits.

10. The method of claim 1 wherein the analyzing step comprises carrying out an electrocardiogram measurement with respect to a heart of the body.

11. The method of claim 1 further comprising the steps of:
emitting first electrical energy within a first band at the first device;
detecting the first electrical energy at the second device;
emitting second electrical energy within a second band at the first device, the second band different from the first band;
detecting the second electrical energy at the second device; and
comparing the detected first electrical energy and the detected second energy with each other, thereby deriving information of interest about the body.

12. The method of claim 11 wherein the step of deriving information of interest about the body comprises inferring a ratio of fluid to non-fluid within the body.

13. The method of claim 11 wherein the step of deriving information of interest about the body comprises inferring blood volume within the body.

14. The method of claim 1 further comprising the step of:
communicating the first data stream from the first device to the second device;
wherein the analyzing step is carried out within the second device.

15. The method of claim 14 wherein the communicating step is carried out by means of infrared light communications or by means of high frequency radio frequency communications.

16. A system comprising a first device and a second device,
the first device comprising a respective electrical signal detector having respective first and second electrodes;
the second device comprising a respective electrical signal detector having respective first and second electrodes;
the first device shaped for encircling a limb of a subject, the first electrode of the first device disposed to be juxtaposed with said limb when the first device encircles the limb, the second electrode of the first device disposed to be more distant from the limb than the first electrode when the first device encircles the limb;
the second device shaped for encircling a limb of a subject, the first electrode of the second device disposed to be juxtaposed with said limb when the second device encircles the limb, the second electrode of the second device disposed to be more distant from the limb than the first electrode when the second device encircles the limb;
the electrical signal detector of the first device responsive to signals at the respective first and second electrodes, yielding a first data stream indicative of a difference between the signals at the respective first and second electrodes;
the electrical signal detector of the second device responsive to signals at the respective first and second electrodes, yielding a second data stream indicative of a difference between the signals at the respective first and second electrodes;
the system further comprising an analysis means, said means responsive to the first data stream and the second data stream, for deriving information of interest about the body.

17. The system of claim 16 where the analysis means is separate from the first device and separate from the second device, the system further comprising:
a communications link from the first device to equipment, and
a communications link from the second device to the equipment.

18. The system of claim 16 wherein the first device further comprises a rechargeable energy storage, the first device further comprising a means converting movement into electrical energy, said electrical energy recharging the rechargeable energy storage.

19. The system of claim 18, wherein the analysis means infers a level of physical activity of the body from the converted electrical energy, and
communicates the inferred level of physical activity external to the first device and external to the second device.

20. The system of claim 16 wherein the first device further comprises an analog-to-digital converter converting analog signals from the respective first and second electrodes into digital data, the first data stream comprising said digital data.

21. The system of claim 19 wherein the analog-to-digital converter has a resolution of at least sixteen bits.

22. The system of claim 16 wherein the first device comprises an emitter controllably emitting first electrical energy within a first band at the first device and controllably emitting second electrical energy within a second band at the first device, the second band different from the first band;
and wherein the second device comprises a detector disposed to detect first electrical energy and the second electrical energy;
the analysis means disposed to compare the detected first electrical energy and the detected second energy with each other, thereby deriving information of interest.

23. The system of claim 16 wherein the first device communicates the first data stream to the second device; and
wherein the analyzing means is within the second device.

24. The system of claim 23 wherein communicating is carried out by means of an infrared light communications channel or by means of a high frequency radio frequency communications channel.

* * * * *